United States Patent [19]
Faiman et al.

[11] Patent Number: 5,153,219
[45] Date of Patent: Oct. 6, 1992

[54] THIOCARBAMATE SULFOXIDE COMPOSITION FOR DETERRING ETHANOL INGESTION

[75] Inventors: Morris D. Faiman, 610 W. 28th Pl., Lawrence, Kans. 66046; Bruce W. Hart; Ajay Madan, both of Lawrence, Kans.

[73] Assignee: Morris D. Faiman, Lawrence, Kans.

[21] Appl. No.: 689,160

[22] Filed: Apr. 22, 1991

[51] Int. Cl.$^5$ ............................................. A61K 31/27
[52] U.S. Cl. ................... 514/478; 514/811; 424/10
[58] Field of Search ............ 558/234, 236; 424/9, 424/10; 514/811, 478

[56] References Cited

U.S. PATENT DOCUMENTS 4,565,689 1/1986 Revici .................................. 424/10

FOREIGN PATENT DOCUMENTS

WO8909208 10/1989 PCT Int'l Appl.

OTHER PUBLICATIONS

C.A. 77, Nilsson, et al., 151635b, (1972).
C.A. 82, Gozzo, et al., 169773h, (1975).
C.A. 103, Showa, et al., 22177k, (1985).
F. Gozzo et al., *Chemistry and Industry*, (1975), pp. 221-226.
T. M. Kitson et al., *Biochem. J.*, 278, (1991), pp. 189-192.
M. D. Faiman et al., *Toxicologist Abstract*; 10, 174 (1990); No. 693.
B. W. Hart et al., *FASEB Journal Abstract*, 4, A744 (1990).
B. W. Hart et al., *Alcohol*, pp. 165-169, (1990).
B. W. Hart et al., *Alcoholism*: Clin. and Exp. Res., 12, 317 (1988).
J. J. Yourick et al., *Alcohol*, 4, pp. 463-467.
J. J. Yourick et al., *Biochem. Pharmacol.*, 38, pp. 413-421, (1989).
B. Johansson et al., *Biochem. Pharmacol.*, 38, pp. 1053-1059, (1989).
B. Johansson, *Pharmacol. and Toxicol.*, 64, pp. 471-474 (1989).
A. Helander et al., *Biochem. Pharmacol.*, 38, pp. 2195-2198, (1989).
E. N. Peterson, *Europ. J. Pharmacol.*, 166, pp. 419-425, (1989).
J. E. Casida et al., *Pesticide Biochem. and Physiol.*, 5, pp. 1-11, (1975).
J. E. Casida et al., *Science*, 184, pp. 572-574, (1974).
J. E. Peachey et al., *J. Clin. Psychopharmacol.*, 1, pp. 368-375, (1981).
M. Faiman et al., *Alcoholism: Clin. and Exp. Res.*, 7, pp. 307-311, (1983).
J. F. Brien et al., *Europ. J. Clin. Pharmacol.*, 14, pp. 133-141 (1978).
P. Klason, *J. Prak. Chemie*, 36, pp. 57-64, (1987).
S. O. Tottmar et al., *Biochem. J.*, 135, pp. 577-586, (1983).
C. O. P. Eriksson et al., *Anal. Biochem.*, 80, pp. 116-124, (1977).

Primary Examiner—Joseph P. Brust
Attorney, Agent, or Firm—Merchant, Gould, Smith, Edell, Welter & Schmidt

[57] ABSTRACT

A method is provided for deterring ethanol ingestion by a human, comprising administering to said human an amount of a compound of the formula $(R^1)(R^2)NC(X)S(O)R^3$ effective to cause the disulfiram-ethanol reaction in said human, wherein $R^1$, $R^2$ and $R^3$ are each ($C_1$-$C_4$) alkyl groups, e.g., methyl, ethyl, propyl, isopropyl, butyl, i-butyl and t-butyl.

15 Claims, 5 Drawing Sheets

THIOCARBAMATE SULFOXIDE COMPOSITION FOR DETERRING ETHANOL INGESTION

BACKGROUND OF THE INVENTION

This invention was made with the assistance of grants from the National Institute on Alcohol Abuse and Alcoholism (Grant No. AA 03577) and the National Institute of General Medical Sciences (Grant No. T32 GM 07775). The Government has certain rights in the invention.

The use of aldehyde dehydrogenase (ALDH) inhibitors is one pharmacotherapeutic approach which has been employed for the treatment of alcohol (ethanol) abuse and alcoholism. Examples of these types of compounds presently used clinically are disulfiram (tetraethylthiuram disulfide) (Antabuse®), and carbimide (citrated calcium carbimide, cyanamide (Temposil®)). Disulfiram is used throughout the world, whereas calcium carbimide has not been approved by the FDA for use in the United States.

The rationale for the use of ALDH inhibitors such as disulfiram for the treatment of alcoholism, is that they block the metabolism of ethanol. Thus, after ethanol ingestion, inhibitors of liver mitochondrial low Km ALDH cause an increase in the formation of acetaldehyde. Clinically, this leads to tachycardia, hypotension, nausea, and other adverse symptoms that are referred to as the disulfiram-ethanol reaction (DER). Although disulfiram is widely used in the treatment of alcoholism, its use is not without controversy. A number of reports have questioned disulfiram's toxicity and its ability to produce a DER that is effective to deter ethanol ingestion.

Although studies have been carried out for over 40 years in an attempt to delineate the mechanism by which disulfiram inhibits ALDH, this mechanism is not completely understood. Most of the studies investigating this inhibition have been carried out in vitro, and it has been implied from those studies that disulfiram-induced inhibition in vivo occurs by a similar mechanism. It has been only recently that an appreciation of disulfiram's metabolism has evolved, allowing for a better understanding of the relationship between disulfiram bioactivation, liver ALDH inhibition, and the DER. Much of the basic data providing this understanding has been generated in the laboratory of Morris D. Faiman. For example, see J. J. Yourick and M. D. Faiman, *Alcohol*, 4, 463 (1987); *Biochem. Pharmacol.*, 38, 413, (1989); and B. W. Hart et al., *Alcohol*, 7, 165 (1990).

As shown in FIG. 1, disulfiram is reduced to diethyldithiocarbamate (DDTC), which is subsequently degraded nonenzymatically to carbon disulfide and diethylamine. DDTC also is methylated to form the ester, diethyldithiocarbamate-methyl ester (DDTC-Me), which then forms S-methyl-N,N-diethylthiolcarbamate (DETC-Me).

B. W. Hart et al., in *Alcohol*, 7, 165 (1990) synthesized DETC-Me and determined that it is a more potent inhibitor of liver mitochondrial low Km ALDH than either DDTC-Me, DDTC or disulfiram. The dose at which 50% ALDH inhibition ($ID_{50}$) occurred after the intraperitoneal (IP) administration of DETC-Me, DDTC-Me or disulfiram was 6.5, 15.5 and 56.2 mg/kg, respectively. The DER produced by DETC-Me in animals is consistent with that seen with disulfiram, DDTC and DDTC-Me. However, Hart et al. also reported that DETC-Me is not an effective in vitro inhibitor of liver mitochondrial low Km ALDH, and concluded that DETC-Me is not the ultimate species responsible for ALDH inhibition.

Therefore, a need exists for simple compounds which are effective to deter alcohol ingestion by inducing the DER at low, non-toxic dosages.

SUMMARY OF THE INVENTION

The present invention provides a method for deterring alcohol ingestion by a human comprising administering to said human a pharmaceutical unit dosage form comprising an amount of a compound of the formula I:

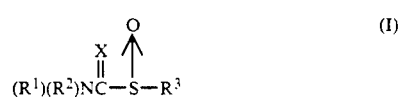

wherein $R^1$, $R^2$ and $R^3$ are individually ($C_1$–$C_4$) alkyl, X is O or S; and the pharmaceutically acceptable salts thereof, which is effective to increase blood acetaldehyde concentration in the presence of ethanol. Novel compounds of formula (I) are also within the scope of the invention. For example, especially preferred compounds of the present invention include those wherein X is O, $R^1$ and $R^2$ are individually ethyl or methyl and $R^3$ is methyl. Most preferably, $R^1 = R^2 =$ methyl or ethyl, e.g., the compound is S-methyl-N,N-diethylthiolcarbamate sulfoxide (DETC-Me sulfoxide) or S-methyl-N,N-diethyldithiocarbamate sulfoxide (DDTC-Me sulfoxide). Preferred compounds within the scope of the invention are substantially more bioactive than disulfiram, or the corresponding unoxidized, dithiocarbamate or thioester compounds. For example, DETC-Me sulfoxide is about twice as effective at inhibiting ALDH in vivo as is DETC-Me. Furthermore, DETC-Me sulfoxide is active in vitro, while DETC-Me is not. Thus, DETC-Me sulfoxide and DDTC-Me sulfoxide may well be ultimate active species resulting from the in vivo metabolism of disulfiram.

Preferred compounds of the invention are (a) potentially less toxic, with fewer side effects than the parent compounds; (b) do not require bioactivation by the P450 liver enzyme system as do the metabolic precursors, and/or (c) produce a rapid, consistent and reliable DER.

Pharmaceutically acceptable salts of the present thiolcarbamate sulfoxides and dithiocarbamate sulfoxides include the nontoxic addition salts of organic and inorganic acids, such as the citrates, bicarbonates, malonates, tatrates, gluconates, hydrochlorides, sulfates, phosphates, and the like. All percentages are weight percentages unless otherwise indicated.

DETAILED DESCRIPTION OF THE INVENTION

Figure 1:
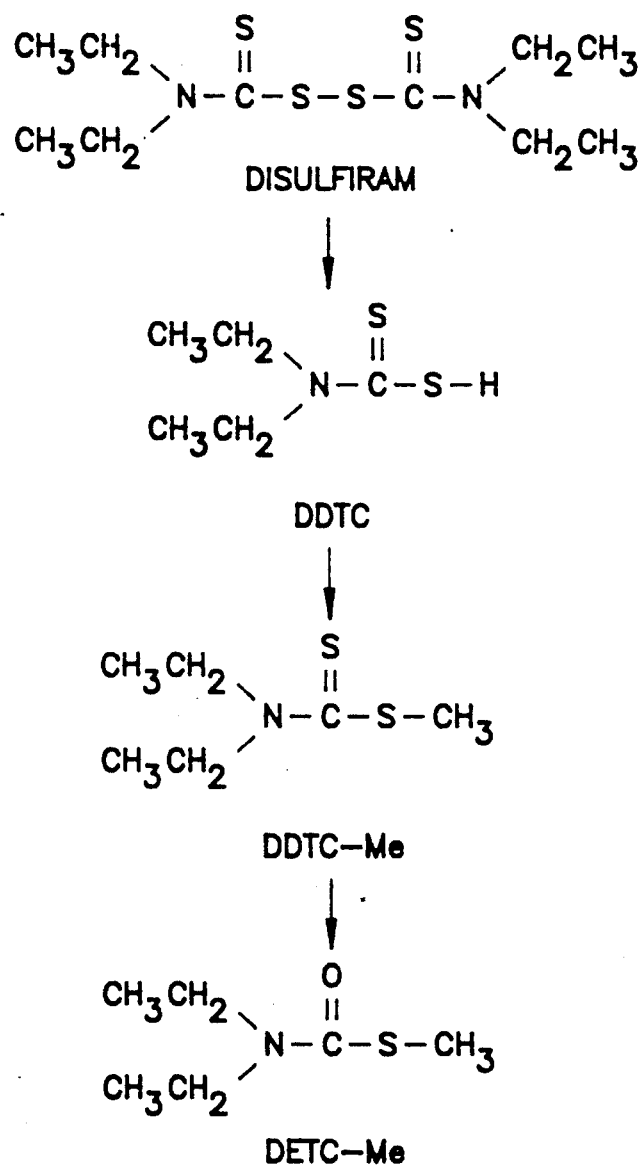
FIG. 1 is a schematic depiction of the in vivo metabolism of disulfiram.

The compounds of formula I, wherein $X=O$ or S, can be readily prepared by periodic oxidation of the corresponding thiol esters of formula II: $(R^1)(R^2)NC(X)SR^3$ wherein X, $R^1$, $R^2$, and $R^3$ are as described hereinabove. In turn, the thiol esters of formula (II) wherein $X=O$, can be prepared by the bubbling carbonylsulfide into a mixture of triethylamine and an amine of the formula $(R^1)(R^2)NH$, wherein $R^1$ and $R^2$ are as described hereinabove, in a suitable solvent, such as t-butanol. In situ methylation with an alkyl iodide $(R^3I)$, wherein $R^3$ is as described above, yields the corresponding thiol ester II. Dithiocarbamates of formula II $(X=S)$ can be prepared as disclosed by M. Faiman et al., *Alcoholism: Clin. and Exp. Res.*, 7, 307 (1983). The final products can be purified by chromatography on silica gel.

In clinical practice, the compounds of formula I, or the salts thereof, will normally be administered orally in the form of a pharmaceutical unit dosage form comprising the active ingredient in combination with a pharmaceutically acceptable carrier which may be a solid, gelled or liquid diluent or an ingestible capsule. A unit dosage of the compound or its salt may also be administered without a carrier material. As examples of pharmaceutical preparations may be mentioned tablets, hard or soft gelatin capsules, aqueous solutions, suspensions, and liposomes and other slow-release formulations, such as shaped polymeric gels. Usually the active substance will comprise between about 0.05 and 99%, or between 0.1 and 95% by weight of the unit dosage form, for example, between about 0.1 and 50% of preparations intended for oral administration.

The amount of the compound of formula I that is administered and the frequency of administration to a given human patient will depend upon a variety of variables related to the patient's psychological profile and physical condition. For evaluations of these factors, see J. E. Peachey, A Review of the Clinical Use of Disulfiram and Calcium Carbimide in Alcoholism Treatment, *J. Clinical Psychopharmacology*, 1, 368 (1981); J. F. Brien et al., *Europ. J. Clin. Pharmacol.*, 14, 133 (1978); and *Physicians' Desk Reference*, Charles E. Baker, Jr., Pub., Medical Economics Co., Oradell, N.J. (41st ed., 1987) at page 632–633. Generally, the dosages of the present compounds will be smaller than that administered in the case of disulfiram which is presently administered at 4–8 mg/kg orally, or than putative dosages of DETC-Me The invention will be further described by reference to the following detailed examples

Example 1 S-Methyl-N,N-Diethylthiolcarbamate (DETC-Me)

DETC-Me was synthesized employing a modification of the method of P. Klason, *J. Prak. Chemie*, 36, 57 (1887). Carbonyl sulfide, produced by dripping saturated KSCN into 48% sulfuric acid, was bubbled into a mixture of 11.3 ml of triethylamine and 7.7 ml of diethylamine in 100 ml of t-butyl alcohol in a 250 ml round bottom flask. The solution was stirred as the gas bubbled through the amine solution, with the reaction proceeding for 15 to 20 hours. The reaction was terminated by adding 5 ml of methyl iodide to form the final methylated product. The reaction mixture turned yellow and 15 to 20 minutes later a white precipitate formed. After 45 min, the reaction mixture was filtered and the alcohol and other volatile materials were evaporated. The remaining oil phase was dissolved in methylene chloride and extracted with 10% HCl, saturated $NaHCO_3$ and brine. The resulting organic phase was dried over sodium sulfate, and evaporated in vacuo. The resulting product was purified by medium pressure liquid chromatography (C-18 Sepralite ® 40 μM, mobile phase 60:40 acetonitrile (Fisher Scientific, HPLC grade): water). Fractions containing the DETC-Me were extracted with methylene chloride. The organic phase was dried with sodium sulfate and solvent removed under reduced pressure. The product (about 4 g) was a pale yellow oil. The structure verified by TLC, NMR [$^1H$ NMR (80 MHz, $CDCl_3$), δ 3.35 (q,J=7 Hz,2H), δ 2.50 (s,3H), δ 1.15 (t,J=8 Hz,3H)], and mass spectroscopy [EIMS M/Z (relative intensity) 147 ($M^-$, 13), 100 (75), 75 (24), 72 (100), 44 (69)].

Example 2 S-Methyl-N,N-Diethylthiolcarbamate Sulfoxide (DETC-Me Sulfoxide).

DETC-Me (600 mg) was added to a suspension of 0.856 g of sodium metaperiodate (Aldrich Chem. Co.) in 8 ml of 1:1 methanol-water at 25° C. After 48 hours of stirring at 25° C., the reaction mixture was extracted with $CH_2Cl_2$. The organic layer was dried with sodium sulfate and the solvent removed under reduced pressure. The crude product was dissolved in a minimum amount of 1:1 acetonitrile-$H_2O$ and purified by medium pressure chromatography (C-18 Sepralite ® 40 μM mobile phase 1:1 acetonitrile-$H_2O$. Fractions containing DETC-Me sulfoxide were pooled and extracted with methylene chloride. The solvent was dried with sodium sulfate and removed under reduced pressure to yield 0.46 g of DETC-Me sulfoxide as a yellowish oil; [$^1H$ NMR (500 MHz, $CDCl_3$) 3.5696–3.4661 (m, 2H), 3.4428–3.3850 (m, 2H), 2.7082 (s.3H), 1.2257 (t, 3H, J=7.12 Hz), 1.1698 (t, 3H, J=7.09 Hz); mass spectroscopy: CIMS ($NH_3$) M/Z (relative intensity), 164 ($M^{+1}$, 13), 148 (3), 100 (100), 72, (86), 44 (82); IR (neat): 2980, 1690, 1420, 1255, 1210, 1065, 1035 $cm^{-1}$].

Example 3 S-Methyl-N,N-Diethyldithiocarbamate Sulfoxide

S-Methyl-N,N-diethyldithiocarbamate sulfoxide (DDTC-Me SO) was prepared from S-Methyl-N,N-diethyldithiocarbamate (DDTC-Me). The synthesis of DDTC-Me was carried out as described by M. D. Faiman et al., *Alcoholism*, 7, 307 (1983). Sodium metaperiodate (200 mg) (Sigma Chemical Co.) was dissolved in 25 ml of 50:50 MeOH:$H_2O$ at 0° C. DDTC-Me (200 mg) was separately dissolved in 2 ml of methanol, and was then cooled to 0° C. before addition to a constantly stirring solution of sodium metaperiodate in MeOH:$H_2O$. The reaction mixture was stirred for 24 hr at 0° C. and then was diluted to 100 ml with cold 0.1M potassium phosphate buffer (pH 7.4). The resulting colorless solution was then extracted with methylene chloride The organic layer was treated with activated charcoal, and the charcoal was removed by filtration through a Celite bed. The solvent was removed under reduced pressure to obtain the crude product which was then purified by preparative HPLC (C-18, 5 micron, 150 mm×10 mm column, Alltech) using 30:70 acetonitrile:H$_2$O (acetonitrile, Fisher Scientific, HPLC grade) at a flow rate of 2.5 ml/min. The fractions containing the DDTC-Me SO were pooled and diluted with four times the original volume with water. The diluted pooled fractions were extracted with methylene chloride. The solvent was dried with sodium sulfate and removed under reduced pressure to yield 50 mg of product a colorless oil; $^1$H NMR (300 MHz, CDCl$_3$) 3.25–3.42 (m, 4H), 2.72 (s, 3H), 1.23 (t, 3H), 1.17 (t, 3H); mass spectoscopy: CIMS (NH$_3$) M/Z, 180 (M+$^1$); IR (neat): 2954, 1668, 1436, 1400, 1317, 1136, 1113, 747 cm$^{-1}$.

Example 4 Evaluation of DETC-Me Sulfoxide and DDTC-Me Sulfoxide as In Vitro Inhibitors of Rat Liver Low Km Aldehyde Dehydrogenase.

1. Drug Concentration. Concentrations of DETC-Me sulfoxide ("DETC-Me SO") studied were 0.2 μM, 2.0 μM, 20 μM and 200 μM. Concentrations of DDTC-Me SO studied were 0.5 μM, 2.5 μM, 10 μM, 25 μM, 50 μM and 100 μM.

2. Animal Liver Preparation. Male Sprague-Dawley derived rats weighing 200–400 g were anesthetized with carbon dioxide and then decapitated. The livers from untreated rats were homogenized in 0.25M sucrose and differential centrifugation carried out to isolate the mitochondrial fraction. The mitochodria were solubilized with sodium deoxycholate, and mitochondrial low Km ALDH activity determined by the method of S.O.C. Tottmar et al., *Biochem. J.*, 135, 577 (1973).

3. In Vitro Incubation. Mitochondria were isolated from the liver of untreated rats as described in section (2) and resuspended in 0.1M phosphate buffer (pH=7.4). Incubations contained 2 mg of mitochondrial protein, to which was added DETC-Me SO or DDTC-Me SO in the concentrations described above. The DETC-Me SO or DDTC-Me SO was dissolved in ethanol and the incubations carried out for one hour. Control incubations contained ethanol alone.

4. Aldehyde Dehydrogenase Analysis. At the end of the incubation, the mitochondria were isolated by centrifugation, resuspended in 0.25M sucrose buffer and solubilized with deoxycholate. Low Km ALDH activity was determined by the method of S.O.C. Tottmar et al., cited above.

Figure 2:
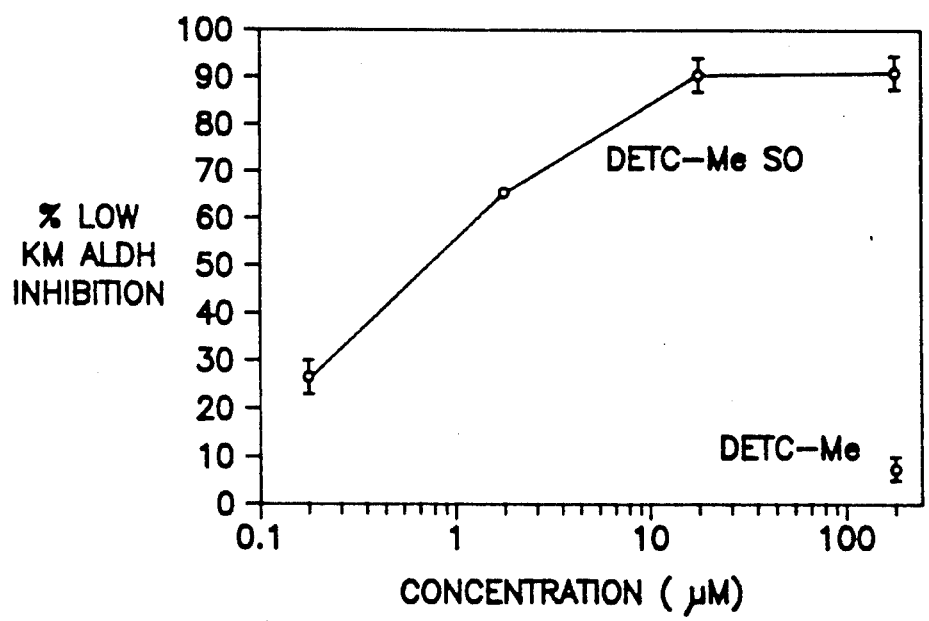
FIG. 2 is a graphical depiction of the in vitro inhibition of rat liver mitochondrial low Km ALDH by DETCMe sulfoxide.

5. Conclusions. FIG. 2 is a plot showing the inhibition of rat liver mitochondrial low Km ALDH in vitro by S-methyl-N,N-diethylthiolcarbamate sulfoxide. The data show that, as the concentration of the DETC-Me SO is increased, inhibition of rat liver mitochondrial low Km ALDH also is increased until maximal inhibition of ALDH is reached. The concentration of DETC-Me SO required for 50% inhibition of the rat liver mitochondrial low Km ALDH is approximately 750 nM. For comparative purposes, 200 μM S-methyl-N,N-diethylthiolcarbamate produces only an 8% inhibition. In both experiments, incubations were carried out for one hour. It is concluded that DETC-Me SO is an extremely potent inhibitor of rat liver mitochondrial low Km ALDH in vitro.

Figure 3:
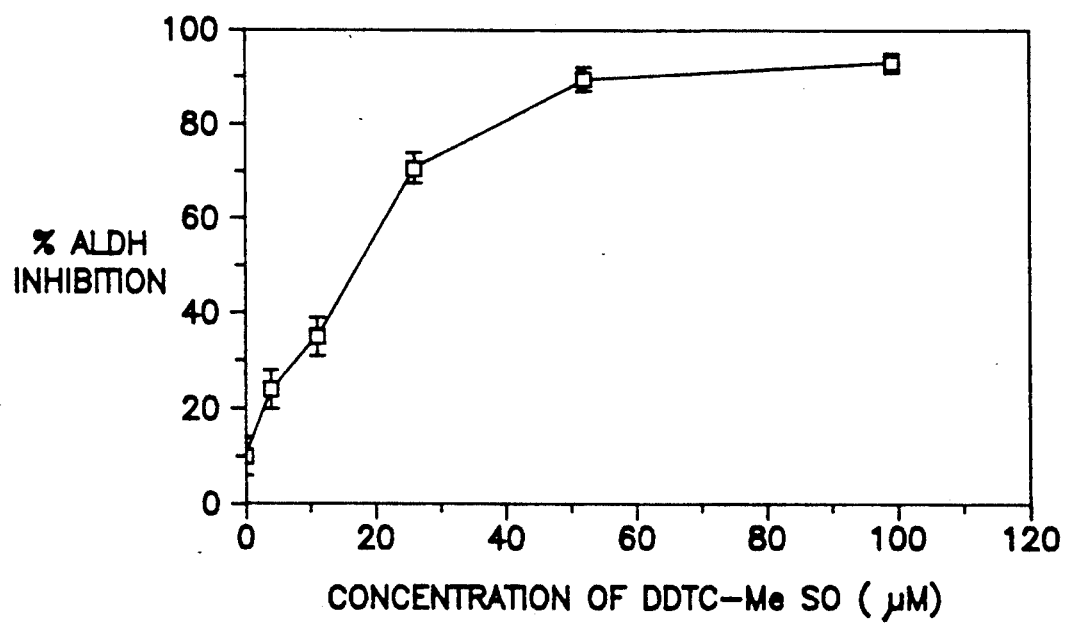
FIG. 3 is a graphical depiction of the in vitro inhibition of rat liver mitochondrial low Km aldehyde dehydrogenase by S-methyl N,N diethyldithiocarbamate sulfoxide (DDTC-Me SO).

FIG. 3 is plot showing the inhibition of rat liver mitochondrial low Km ALDH in vitro by S-methyl-N,N-diethyldithiocarbamate sulfoxide. The concentration of DDTC-Me SO required for 50% inhibition is about 15 μM.

Example 5 Liver Aldehyde Dehydrogenase Determination In Vivo

1. Drug Doses. Doses of DETC-Me SO studied were 1.3 mg/kg, 2.6 mg/kg, 5.2 mg/kg, 10.3 mg/kg and 20.6 mg/kg.

2. Animals. Male Sprague Dawley derived rats weighing 200–400 g were used. The rats were bred from a resident colony maintained in the Animals Care Unit at the University of Kansas. Rats were maintained on a 12-hour light-dark cycle with access to food and water ad lib until the night before an experiment, at which time food was removed. Animals were fasted for 12 hours prior to drug administration.

Figure 4:
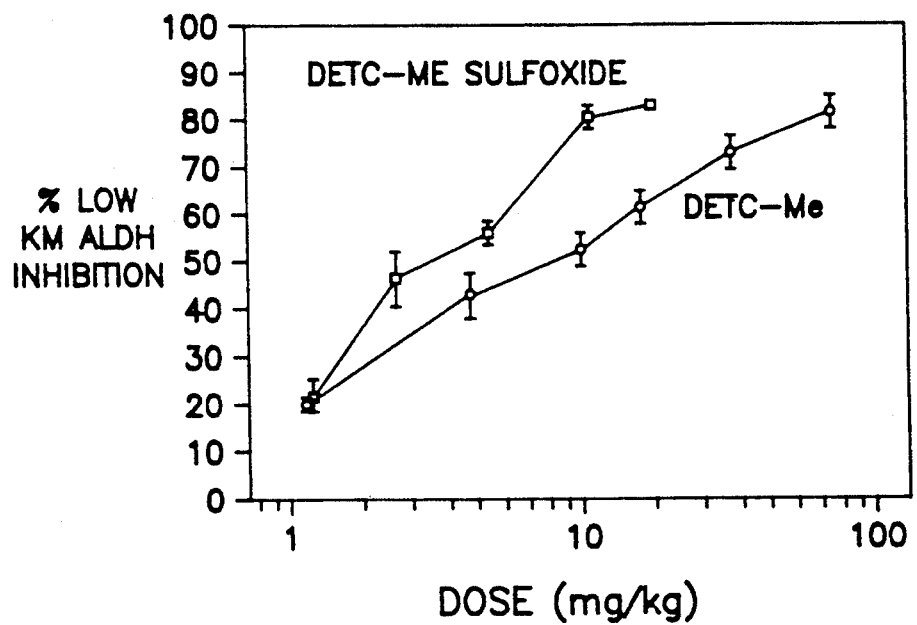
FIG. 4 is a graphical depiction of the inhibition of rat liver mitochondrial low Km ALDH, following the administration of various doses of DETC-Me sulfoxide and DETC to male rats.

3. Timing. In these in vivo studies, rats were fasted 12 hours before beginning the experiment. All experiments were carried out in the morning. Rats were treated with the doses of DETC-Me SO or DETC-Me described above, which were dissolved in polyethylene glycol 200. Eight hours later, the rats were anesthetized with carbon dioxide and then decapitated. The liver was quickly removed and the low Km aldehyde dehydrogenase determined. Each data point on FIG. 4 represents an average of four rats. Control rats were treated with corn oil vehicle only, and each control data point also represents an average of four rats.

4. Aldehyde Dehydrogenase Determination. The liver from drug-treated and control rats was homogenized in 0.25M sucrose and differential centrifugation was carried out to isolate the mitochondrial fraction. The mitochondria were solubilized with sodium deoxycholate, and mitochondrial low Km and total (high and low) aldehyde dehydrogenase activity determined by the method of S.O.C. Tottmar et al., cited above.

5. Conclusions. FIG. 4 is a plot showing the inhibition of rat liver mitochondrial low Km ALDH after the administration of various doses of S-methyl-N,N-diethylthiolcarbamate sulfoxide (DETC-Me SO) and DETC-Me to male rats. The data show that as the administered dose of DETC-Me SO is increased, there is a greater degree of rat liver mitochondrial low Km ALDH inhibition. The dose of DETC-Me SO required to inhibit 50% of the low Km ALDH is 3.6 mg/kg intraperitoneal (IP). For comparative purposes, DETC-Me requires a dose of 6.5 mg/kg IP to produce a comparable degree of low Km ALDH inhibition. Furthermore, the dose of disulfiram which inhibits 50% of the rat liver mitochondrial low Km ALDH is 56.2 mg/kg IP. Therefore, DETC-Me SO is substantially more potent as a rat liver mitochondrial low Km ALDH inhibitor than either disulfiram or any of the other disulfiram metabolites shown on FIG. 1.

Example 6 Plasma Acetaldehyde Determination

Rats maintained as described in Ex. 4, fasted for 18 hours, were given 10.3 mg/kg of the DETC-Me SO intraperitoneally, dissolved in polyethylene glycol 200 and then challenged eight hours later with a dose of ethanol (1 g/kg; 20% v/v) also administered intraperitoneally. The rats were anesthetized with phenobarbital 30 minutes after alcohol administration and blood was taken by aortic puncture, being drawn into a heparinized syringe. Plasma acetaldehyde was determined by the method of C.O.P. Eriksson et al., *Anal. Biochem.*, 80, 116 (1977). Plasma concentrations were determined based on a standard curve obtained with known concentrations of acetaldehyde. Control rats were treated with 1 ml/kg of polyethylene glycol 200.

Figure 5:
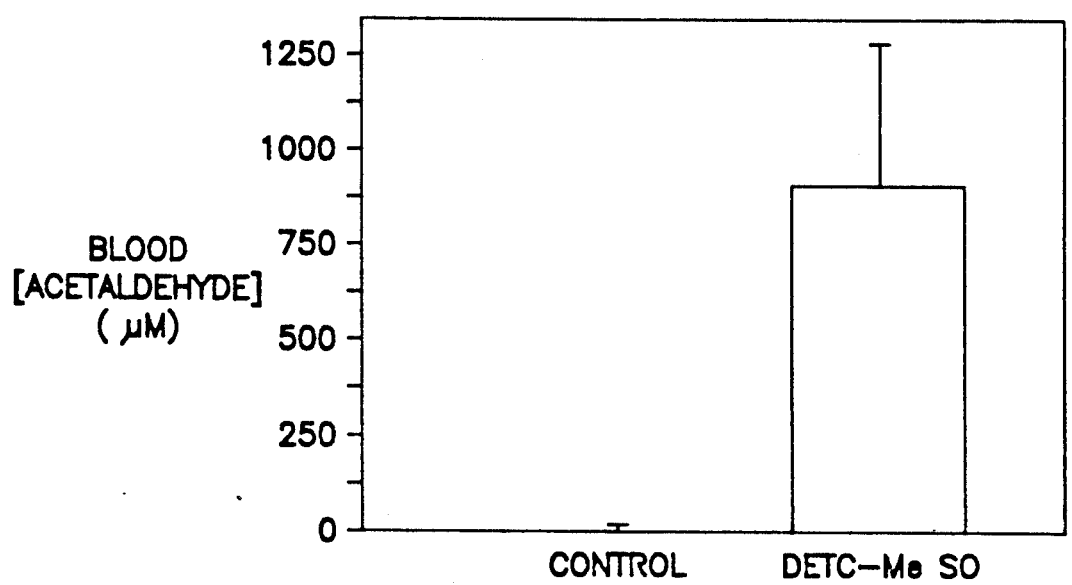
FIG. 5 is a graphical depiction showing the increase in blood acetaldehyde in rats after administration of DETC-Me sulfoxide, followed by administration of i.p. ethanol.

The data in FIG. 5 show a large increase in plasma acetaldehyde after the IP administration of 10.3 mg/kg of S-methyl-N,N-diethylthiolcarbamate sulfoxide dissolved in polyethylene glycol 200, to male rats which were then challenged with 1 g/kg ethanol (20% v/v) IP 30 minutes later. Plasma acetaldehyde increased to approximately 900 μM. Control rats received polyethylene glycol 200 only, and were then challenged with 1 g/kg ethanol IP. In these controls, plasma acetaldehyde was barely detectable. It is concluded that DETC-Me SO can markedly increase plasma acetaldehyde after an ethanol challenge. The increase in acetaldehyde is believed to be responsible for initiating the disulfiram-ethanol reaction, which deters further alcohol consumption.

All patent documents and publications cited herein are incorporated by reference.

The invention has been described with reference to various specific preferred embodiments and techniques. However, it should be understood that many variations and modifications may be made while remaining within the spirit and scope of the invention.

What is claimed is:

1. A method for deterring ethanol ingestion by a human comprising administering to said human a pharmaceutical unit dosage form comprising an amount of a compound of the formula:

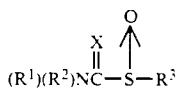

wherein $R^1$, $R^2$ and $R^3$ are individually $(C_1-C_4)$ alkyl, X is O or S, and the pharmaceutically acceptable salts thereof, which is effective to increase the blood acetaldehyde concentration of said human in the presence of ethanol.

2. The method of claim 1 wherein X is S.
3. The method of claim 1 wherein X is O.
4. The method of claim 1 wherein $R^1$ and $R^2$ are individually methyl or ethyl.
5. The method of claim 4 wherein $R^3$ is methyl.
6. The method of claim 4 wherein the compound is S-methyl-N,N-diethylthiolcarbamate sulfoxide.
7. The method of claim 2 wherein the compound is S-methyl-N,N-diethyldithiocarbamate sulfoxide.
8. A pharmaceutical unit dosage form comprising an amount of a compound of the formula:

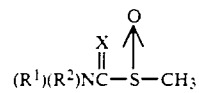

wherein $R^1$ and $R^2$ are individually methyl or ethyl, X is S or O, and the pharmaceutically-acceptable salts thereof; in combination with a pharmaceutically-acceptable carrier, wherein said amount is effective to increase the blood acetaldehyde concentration of a human in the presence of ethanol following administration thereto.

9. The pharmaceutical unit dosage form of claim 8, wherein the compound is S-methyl-N,N-diethylthiolcarbamate sulfoxide.
10. The pharmaceutical unit dosage form of claim 8, wherein the compound is S-methyl-N,N-diethyldithiocarbamate sulfoxide.
11. The pharmaceutical unit dosage form of claim 8 wherein $R^1 = R^2 =$ ethyl.
12. The pharmaceutical unit dosage form of claim 8 wherein X is O.
13. The pharmaceutical unit dosage form of claim 8 wherein X is S.
14. The pharmaceutical unit dosage form of claim 8 wherein the pharmaceutically-acceptable carrier is a liquid diluent.
15. The pharmaceutical unit dosage form of claim 8 wherein the pharmaceutically acceptable carrier is an ingestible capsule.

* * * * *